US00RE44603E

(19) United States
(12) Reissued Patent
Cody et al.

(10) Patent Number: US RE44,603 E
(45) Date of Reissued Patent: Nov. 19, 2013

(54) ATMOSPHERIC PRESSURE ION SOURCE

(75) Inventors: Robert B. Cody, Portsmouth, NH (US); James A. Laramee, Edgewood, MD (US)

(73) Assignee: Jeol USA, Inc, Peabody, MA (US)

(21) Appl. No.: 13/278,778

(22) Filed: Oct. 21, 2011 (Under 37 CFR 1.47)

Related U.S. Patent Documents

Reissue of:
(64) Patent No.: 6,949,741
Issued: Sep. 27, 2005
Appl. No.: 10/732,205
Filed: Dec. 10, 2003

U.S. Applications:
(63) Continuation of application No. 11/858,682, filed on Sep. 20, 2007, now Pat. No. Re. 43,078.

(60) Provisional application No. 60/460,179, filed on Apr. 4, 2003.

(51) Int. Cl.
*H01J 49/10* (2006.01)
*H01J 49/04* (2006.01)

(52) U.S. Cl.
CPC ..... *H01J 49/0459* (2013.01); *H01J 49/10* (2013.01)
USPC ..... 250/288; 250/423 R; 250/424; 356/316

(58) Field of Classification Search
USPC ..... 250/288, 423 R, 424; 356/316
See application file for complete search history.

(56) References Cited

U.S. PATENT DOCUMENTS

| | | | | |
|---|---|---|---|---|
| 4,546,253 | A * | 10/1985 | Tsuchiya et al. | 250/288 |
| 5,192,865 | A * | 3/1993 | Zhu | 250/288 |
| 5,684,300 | A * | 11/1997 | Taylor et al. | 250/286 |
| 6,124,675 | A * | 9/2000 | Bertrand et al. | 315/111.91 |
| 6,225,623 | B1 * | 5/2001 | Turner et al. | 250/286 |
| 6,949,741 | B2 * | 9/2005 | Cody et al. | 250/288 |
| 7,112,785 | B2 * | 9/2006 | Laramee et al. | 250/288 |
| 7,138,626 | B1 * | 11/2006 | Karpetsky | 250/288 |
| 7,569,812 | B1 * | 8/2009 | Karpetsky et al. | 250/282 |
| 7,893,408 | B2 * | 2/2011 | Hieftje et al. | 250/423 R |
| RE43,078 | E * | 1/2012 | Cody et al. | 250/288 |
| 2002/0185593 | A1 * | 12/2002 | Doring | 250/287 |

OTHER PUBLICATIONS

Declaration under 37 C.F.R. 1.132 of Dr. Gary Hieftje from U.S. Appl. No. 11/980,843.*
Kiichiro Otsuka et al, "An Interface for Liquid Chromatograph/Liquid Ionization Mass Spectrometer", Analytical Sciences, Oct. 1988, vol. 4, pp. 467-472.*

(Continued)

*Primary Examiner* — Jack Berman
(74) *Attorney, Agent, or Firm* — Sci-Law Strategies, PC

(57) ABSTRACT

A non-radioactive atmospheric pressure device for ionization of analytes comprises an atmospheric pressure chamber having an inlet for carrier gas, a first electrode at one end, and a counter-electrode at the other end of the chamber for creating an electrical discharge in the carrier gas thus creating metastable neutral excited-state species. Optionally, a grid is provided to generate electrons or ions by contact with the excited-state species. The carrier gas containing the excited-state species or the electrons generated therefrom is directed at an analyte at atmospheric pressure near ground potential to form analyte ions.

7 Claims, 11 Drawing Sheets

(56) References Cited

OTHER PUBLICATIONS

Jianguo Zhao et al., "Liquid Sample Injection Using an Atmospheric Pressure Direct Current Glow Discharge Ionization Source", Analytical Chemistry, Jul. 1, 1992, vol. 64, No. 13, pp. 1426-1433.*
Nancy Leymarie et al., "Negative Ion Generation Using a MAB Source", presented at the Annual Meeting of the American Society of Mass Spectrometry, 2000.*
C.A. Hill et al., "A pulsed corona discharge switchable high resolution ion mobility spectrometer- mass spectrometer", Analyst, 2003, 128, pp. 55-60.*
Christine N. Dalton et al., "Electrospray-Atmospheric Sampling Glow Discharge Ionization Source for the Direct Analysis of Liquid Samples", Analytical Chemistry, Apr. 1, 2003, vol. 75. No. 7, pp. 1620-1627.*

* cited by examiner

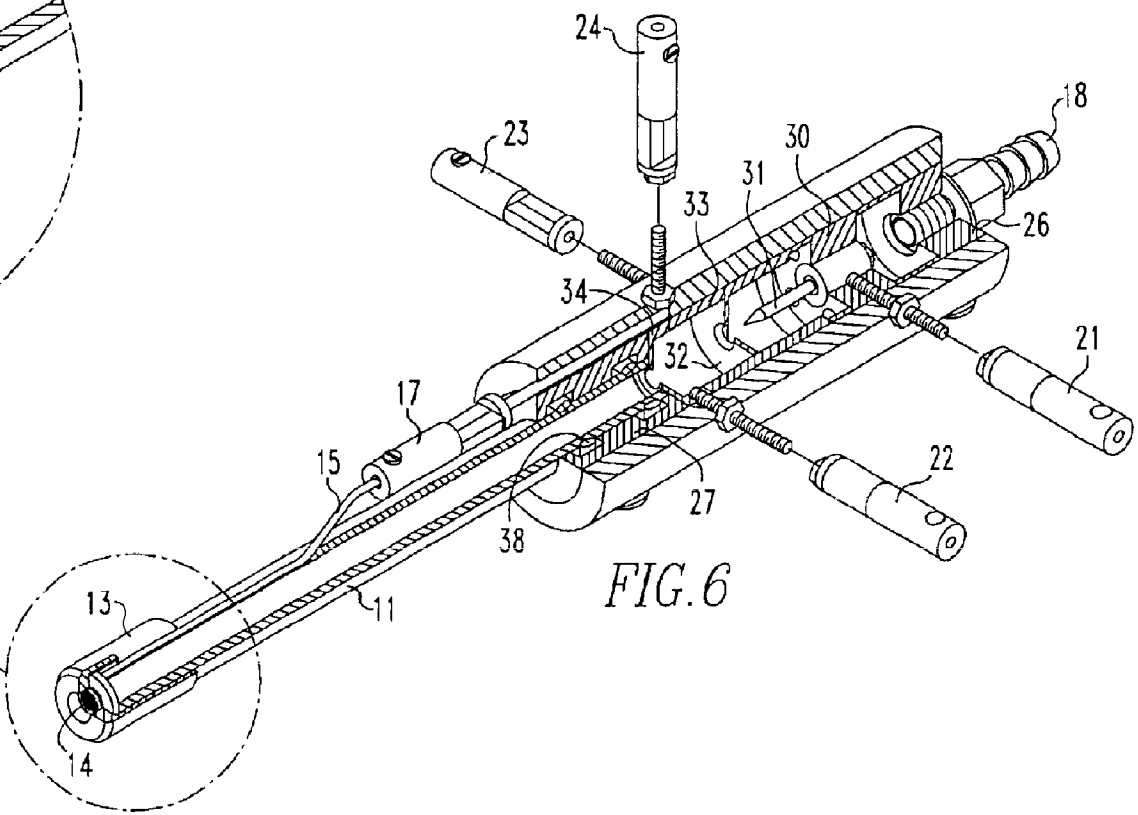
FIG. 6
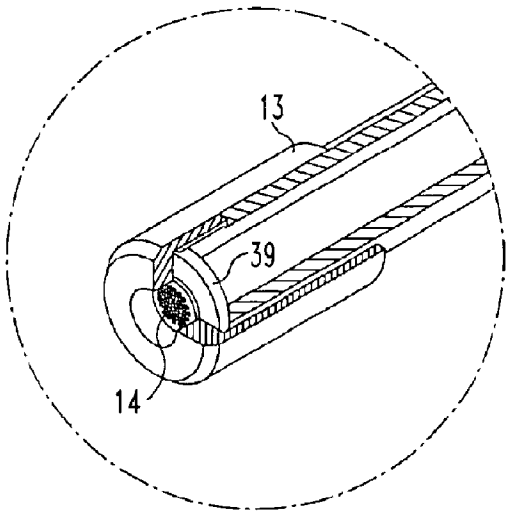
FIG. 7
FIG. 7

HEXAFLUOROBENZENE AT C3

AIR AT C3 NEGATIVE IONS TRAPPED

ROOM AIR AT C3

NITROBENZENE-NEGITIVE ION MODE

NITROMETHANE-POSITIVE ION MODE

NITROBENZENE-POSITIVE ION MODE

BACKGROUND (AIR) OBSERVE $O_2^-$, $HCO_2^-$, $CO_3^-$

ETHYLMETHYLPHOSPHONATE OBSERVE $[M-H]^-$ AND $[2M-H]^-$

DIETHYLMETHYLPHOSPHONATE OBSERVE $[M-C_2H_5]^-$, $[2M-H]^-$, $[2M+O_2-H]^-$

TNT NEGATIVE-ION, HEADSPACE, NO HEAT. SEE M⁻ AND [M-NO]⁻ AND OTHER CONTAMINANTS

ATMOSPHERIC PRESSURE ION SOURCE

Matter enclosed in heavy brackets [ ] appears in the original patent but forms no part of this reissue specification; matter printed in italics indicates the additions made by reissue.

CROSS REFERENCE TO RELATED APPLICATION

This application discloses subject matter disclosed in Provisional Patent Application No. 60/460,179, filed Apr. 14, 2003, and the benefits of 35 U.S.C. § 119(e) are claimed. *This is an application for reissue of U.S. Pat. No. 6,949,741 and claims benefit under 35 U.S.C. §120 as a continuation of application Ser. No. 11/858,682 filed Sep. 20, 2007 which reissued as U.S. Pat. No. Re. 43,078.*

BACKGROUND OF THE INVENTION

1. Field of the Invention

This invention relates to atmospheric ionization of analytes with metastable atoms and molecules. Metastable atoms and molecules (M*) are excited-state species with long lifetimes. Metastable species are produced in corona or glow electrical discharges. Other methods of producing excited-state species include electron impact, photoionization, and controlled interaction of high energy particles with a reactant species. Collisions between excited-state species and ground-state species can result in ionization of the ground-state species and release of electrons by a process known as Penning ionization, for example:

$$M^*+N \rightarrow N^+ + M + e^- \qquad \text{Equation 1}$$

2. Description of Related Art

Regulatory and safety issues related to the use of radioactive materials, such as $^{63}Ni$, $^{241}Am$, and $^{3}H$, among others, have led to a search for non-radioactive ion sources for analytical instruments, such as ion mobility spectrometers. (See Turner et al. U.S. Pat. No. 6,225,623 entitled "Corona Discharge Ion Source for Analytical Instruments" and Doring U.S. Patent Application Publication No. 2002/0185593 entitled "Ion Mobility Spectrometer with Non-Radioactive Ion Source".)

Certain available corona discharge ion sources for atmospheric pressure ionization (API) mass spectrometers or ion mobility spectrometers (IMS) or chemical agent monitors (CAM) introduce the analyte (including solvent, air, and other contaminants) into the region containing a discharge needle. This leads to several problems:

1. The presence of oxygen or other contaminants in the air leads to degradation of the electrodes.

2. It can be difficult to maintain the discharge in the presence of contaminants, requiring a high electrical potential or pulsed potentials.

3. A corona discharge in air leads to the formation of species, such as $NO_2^-$, $NO_3^-$, and related cluster ions. These ions can cause a loss of sensitivity for analyte ions (C. A. Hill and C. L. P. Thomas, Analyst, 2003, 128, pp. 55-60) and can interfere with the detection of $NO_2^-$ and $NO_3^-$ produced from analytes containing nitro functional groups, such as nitro explosives or in the case of chloride ion interference with chlorate propellants and rocket motors or phosphate interference with chemical warfare-related compounds.

4. Introducing air and analyte into the discharge region limits the possibilities for controlling the nature of the chemical background to control the ion-formation chemistry.

Taylor et al. U. S. Pat. No. 5,684,300 entitled "Corona Discharge Ionization Source" and Turner et al. U.S. Pat. No. 6,225,623 B1 entitled "Corona Discharge Ion Source for Analytical Instruments" describe corona discharge ion sources, but do not describe a means for separating the region where the discharge occurs from the region where the analyte is introduced. See also Zhao et al. entitled "Liquid Sample Injection Using Atmospheric Pressure Direct Current Glow Discharge Ionization Source," Anal. Chem., 64, pp.1426-1433, 1992.

Bertrand et al. U.S. Pat. No. 6,124,675 entitled "Metastable Atom Bombardment Source" discloses a metastable atom source operating at reduced pressure for generating ions in a mass spectrometer. The device described requires substantially reduced pressures and does not describe means for using metastable atoms for atmospheric pressure ionization mass spectrometry or ion mobility spectrometers.

Tsuchiya et al. U.S. Pat. No. 4,546,253 entitled "Apparatus for Producing Sample Ions" describes a method for using metastable atoms to produce ions from a sample introduced at the tip of an emitter needle downstream from the corona discharge. This technique requires that the sample be placed on or near an intense electric field emitter needle. See also Otsuka et al. entitled "An Interface for Liquid Chromatograph/Liquid Ionization Mass Spectrometer," Analytical Sciences, Vol. 4, Oct. 1988. The present invention avoids use of an emitter needle at high electrical potential placed downstream of the corona discharge source. Further, the present invention provides a means of sampling neutral analyte molecules without the restriction of relocating the analyte from the surfaces on which they are attached. For example, cocaine from cash currency, and chemical/biological warfare agents from surfaces of military interest can be sampled directly and in situ without swabbing or solvent washing the surface. Each time sample is relocated, analyte molecules are lost (30 to 100% for trace-level concentrations). Therefore, direct surface sampling is always preferred.

SUMMARY OF THE INVENTION

Briefly, according to this invention, there is provided an atmospheric pressure ionization source or interface comprising: a first atmospheric pressure chamber having an inlet for carrier gas, a first electrode, and a counter-electrode for creating a corona or glow electric discharge in the carrier gas causing the formation of neutral excited-state metastable species; a second atmospheric pressure chamber having a port in communication with the first chamber; and an optional third atmospheric pressure chamber having a port in communication with the second chamber, there being a lens electrode about said port between the second and third chambers, the third chamber having an outlet port for the carrier gas and an optional electrode at the outlet port. The discharge is confined to the first chamber. Preferably, the first electrode and ports are substantially aligned. A power supply is provided for maintaining selected potentials on each electrode. There may be a conductive grid at the outlet of the second or third chamber. The third chamber may advantageously be an elongated glass tube that is removably inserted into a socket in the second chamber.

The atmospheric pressure source or interface can be used to form positive or negative ions for use with spectrometers or other instruments which operate in the positive or negative ion mode. Typically, negative and positive ions are both formed when the analyte is brought into contact with the excited state species. Some analytes are electrophilic and tend to capture electrons to produce negatively charged analyte ions that allow detection and identification of these analytes. Others have a greater affinity for protons or positive ions and become ionized by picking up a proton $[M+H]^+$,for example. This will guide the selection of an instrument in a positive or negative ion mode.

Preferably, the power supply permits the lens electrode and the electrode at the outlet port to switch polarity without switching the polarity of the first electrode and the counter-electrode. This will enable rapid selection of the ionization source between positive and negative ion modes. The first electrode and counter-electrode must be maintained at potentials sufficient to induce an electrical discharge. The counter-electrode also serves to filter ionized species. The potential difference between the first electrode and counter-electrode necessary for the formation of a discharge depends on the carrier gas and the shape of the first electrode, and is usually several hundreds of volts, say 400 or 1,200. But for small electron structures such as those used in flat-screen plasma TV's, a few volts is sufficient. The first electrode, for example, a needle electrode, may have either a positive or negative potential. The counter-electrode is normally grounded or of polarity opposite to the needle electrode. This is the case whether operating in the positive ion or negative ion mode. In the positive ion mode, the lens electrode may be between ground potential and a few hundred positive volts to filter out negative ions in the carrier gas. Also, in the negative ion mode, the lens electrode may be between ground and minus a few hundred volts to filter out positive ions in the carrier gas.

According to a first embodiment of this invention, the apparatus described in the preceding paragraph is placed with the outlet of the third chamber close to the entrance of a charged particle detector in a positive ion mode, such as a mass spectrometer, an ion mobility spectrometer, or a chemical agent monitor. The electrodes are placed in the positive ion mode. The gas containing excited-state species emerging from the outlet port of the third chamber is directed through or at an analyte positioned near the entrance to the detector operated in the positive ion mode. The metastable species in the carrier gas react with the analyte to form positive ions for analysis. Analyte molecules undergo ion molecule reactions to form species such as $[M+H]^+$. The form of the analyte may be a vapor from an open vial, in solid form on a surface, or in the form of an aspirated liquid, for example.

According to a second embodiment of this invention, the apparatus described above is placed with the outlet of the third chamber close to the entrance to a charged particle detector. The electrodes are placed in the negative ion mode. The gas containing exited-state species emerging from the outlet port of the third chamber is directed through or at an analyte positioned near the entrance to the detector operated in the negative ion mode. The metastable species in the carrier gas react with the analyte to form negative ions for analysis. The form of the analyte may be a vapor from an open vial, in solid form on a surface, or in the form of an aspirated material, for example.

According to a third embodiment of this invention, the apparatus described above is used in a "sniffer" mode with the outlet of the third chamber close to the entrance of a charged particle detector. The electrode at the outlet may comprise a grid and is maintained at ground or negative potential or at an AC potential offset by a DC voltage to induce dissociation of the reactive species to provide a source of electrons as the metastable species collide with the grid. The resulting electrons are rapidly cooled (slowed) to thermal energies by collisions with the gas molecules. The electrodes are placed in the negative ion mode. The gas containing electrons emerging from the outlet port of the third chamber is directed through or at an atmospheric pressure analyte not in an intense electric field and positioned near the entrance to a charged particle detector, such as a mass spectrometer or ion mobility spectrometer, either of which is operated in the negative ion mode. The electrons in the carrier gas are captured by the analyte to form negative ions that are cooled by gas collisions. The form of the analyte may be a vapor from an open vial, in solid form on a surface, or in the form of a static or aspirated liquid, for example.

A fourth embodiment is similar to the third "sniffer" mode embodiment except that the grid electrode is maintained positive and the gas emerging from the outlet forms positive ions with the analyte for analysis in the positive ion mode.

According to a fifth embodiment of this invention, there is provided an atmospheric pressure ionization source or interface comprising: a first atmospheric pressure chamber having an inlet for carrier gas, an electrode therein, and a counter-electrode for creating a corona or glow discharge in the carrier gas creating metastable species, ions, electrons, hot atoms and molecules, and radicals; a second atmospheric pressure chamber adjacent the first chamber having a port into the first chamber and having an optional inlet and optional outlet for cooling or reactant gases; and a third atmospheric pressure chamber adjacent the second chamber having a port into the second chamber and having an inlet for analyte gas and an outlet port for ionized products of the interaction of the metastable species and the analyte gas, the electrode and ports being substantially aligned.

According to a sixth embodiment of this invention, there is provided an atmospheric pressure ionization source or interface comprising: a first chamber having an inlet for carrier gas, an electrode therein, and a counter-electrode for creating a glow or corona discharge in the carrier gas creating metastable species; and a second chamber adjacent the first chamber having an outlet port for electrons and/or metastable species, the electrode and ports being substantially aligned.

By atmospheric pressure in this specification and the appended claims is meant pressures near ambient pressures, say 400 to 1,400 Torr. This would include pressurized aircraft and submerged submarines. For laboratory use, ambient pressures may fall within the range 700 to 800 Torr.

The carrier gas may be heated prior to introduction into the interface or while in the interface to facilitate vaporization or desorption of the analyte into the gas phase from surfaces. It is preferable to provide an adjustable regulator for adjusting the gas pressure to control the speed of ionizing electron energy since electrons embedded in the gas stream will be carried along and accelerated by changing gas pressures. Energy resolved spectra may be achieved in this fashion.

BRIEF DESCRIPTION OF THE DRAWINGS

Further features and other objects and advantages will become clear from the following detailed description made with reference to the drawings in which:

FIG. 6 is a broken away perspective view similar to FIG. 5;

FIG. 7 is a detail from the perspective view of FIG. 6;

DESCRIPTION OF THE PREFERRED EMBODIMENTS

Figure 1:
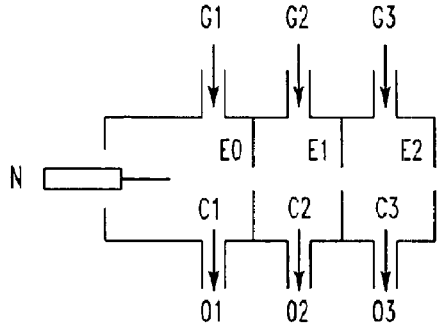
FIG. 1 is a schematic diagram of an atmospheric pressure source comprising aligned chambers C1, C2, and C3 according to the present invention.

A generalized implementation of the present invention is shown schematically in FIG. 1. This device provides an electrode N, for example, a needle electrode, to which an electrical potential can be applied in a first atmospheric pressure chamber C1 into which a carrier gas can be introduced through gas inlet G1 and flow out of a gas-closeable outlet O1. The electrode N may be a point, line, plane, or curved-shape electrode. A needle electrode is an example of a point electrode, and a trim blade is an example of a line electrode. Indeed, there may be multiple needles or other electrodes of the same polarity in the first atmospheric chamber, an arrangement especially useful for chemical agent monitors. A corresponding increase in detection sensitivity is observed when multiple electrodes (N) are used. The counter-electrode E0 contains a hole through which gas and charged particles can pass. It is set to a potential (for example, ground potential) that allows a corona or glow electrical discharge to be established between the electrode N and counter-electrode E0. The electrode may be either a cathode establishing a negative potential or an anode establishing a positive potential. In the electrical discharge, positive ions, electrons, and metastable excited-state atoms are formed. An additional electrode E1 is placed at the exit of an optional second chamber C2 with closeable gas inlet G2 and closeable gas outlet O2. Electrode E1 also defines the entrance to third chamber C3 where a final electrode E2 is positioned at the exit.

In one current implementation, carrier gas is introduced from a gas cylinder into chamber C1 at a positive pressure. This causes flow of metastable excited-state atoms into chambers C2 and C3. In this implementation, the chambers have a volume of about one cubic centimeter. The orifices between chambers are about 3 mm in diameter and the flow through the orifices is on the order of a few milliliters per minute.

The carrier gases that have been used by the Applicants are helium and nitrogen. P-10 gas (90% argon +10% methane) and He/Ne mixtures are potential carrier gases. Also under consideration are argon and krypton. Indeed, any gas or mixture of gases with a metastable state lying higher than a state of the analyte is a potential carrier gas.

The corona or glow electrical discharge occurs in chamber C1. Chamber C2 provides an optional buffer region between chambers C1 and C3, and provides an option for introducing a separate cooling gas or a reactant gas. Cooling gases comprise, for example, gases that would be ionized by metastable atoms to produce a positive ion and electron. The electron would be thermalized by further collisions. Carbon dioxide, methane, and air are examples of cooling gases. Reactive gases are those that favor distinctive ion peaks by ion-molecule reactions. Typically, a small amount of reactive gas, such as ammonia (to promote ammonium ion attachment for positive ions), or a gas that produces chloride ions (e.g., methylene chloride, chloroform, or carbon tetrachloride for negative ions), can be added to the cooling gas. Chloride ion addition has been shown to drastically enhance the detection of polynitro explosives by several orders of magnitude. The analyte may be introduced into chamber C3 and ions of analyte are extracted through a port in electrode E2 into the mass spectrometer atmospheric pressure interface or into the ion mobility spectrometer drift region. The device, or any part of it, can be heated to facilitate the analysis of compounds with low vapor pressures and to reduce sample carryover.

Figure 2:
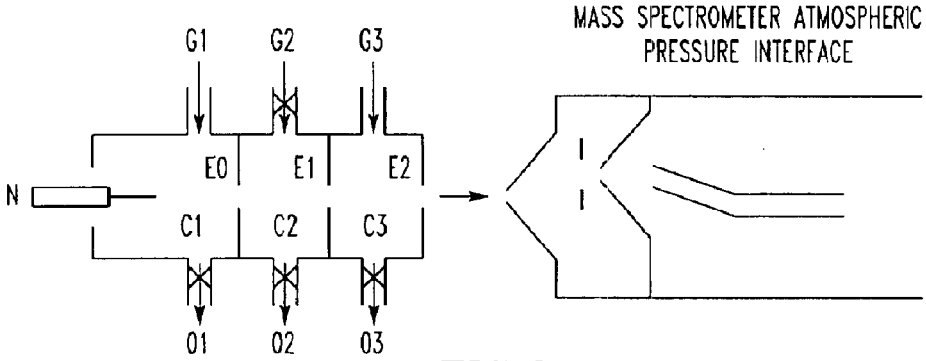
FIG. 2 is a schematic diagram of the atmospheric pressure source associated with a mass spectrometer.

FIG. 2 shows a specific configuration of the atmospheric ionization source for comparative operation where a carrier gas (for example, nitrogen or helium) flows into first chamber C1, passes through intermediate chamber C2, and exits final chamber C3 through a port in electrode E2. All gas outlets O1, O2, and O3 are closed and inlet G3 is sealed with a septum to permit the injection of analyte vapor with a gas-tight syringe. The ions and metastable gas molecules flow along the axis from needle electrode N through the ports in electrodes E0, E1, and E2.

The carrier gases with which Applicants have practiced the invention are helium and nitrogen. Both have high first electron ionization potentials and are not reactive with other elements or compounds at room temperature and pressure. Other noble gases, such as argon, krypton, and xenon, are suitable carrier gases for this reason.

The discharge according to the present invention is either a corona discharge or a glow discharge. It is understood that in electrical discharges, electrons are accelerated into the atoms and molecules of the carrier gas causing additional electrons to be freed and accelerated in a cascading fashion. Collisions in addition to freeing electrons and creating positive ions transfer energy to atoms and molecules to create metastable excited-state species. A glow discharge is a luminous electrical discharge without sparks through a gas. A corona is a faint glow adjacent to the surface of an electrical conductor at high voltage. Typically, glow discharges require a large potential to initiate but a lower voltage to be sustained following "break down". The internal resistance of the power supply for the needle electrode and other factors limit the current in the discharge. Higher currents that might result in sputtering or arcing would not be according to the present invention.

Figure 9:
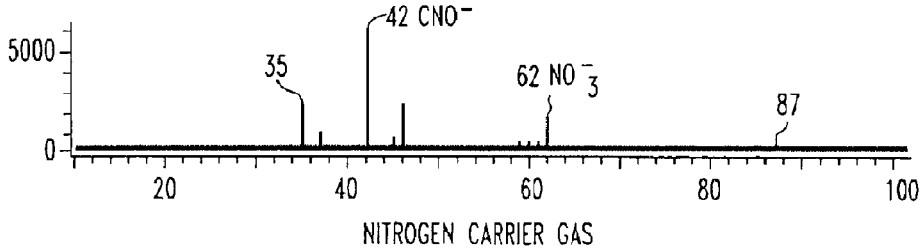
FIG. 9 is a mass spectrum of nitrogen carrier gas introduced into the discharge region of chamber C1 of FIG. 2.

The device shown schematically in FIG. 2 was placed at the entrance cone ("orifice") of the atmospheric pressure interface of the JEOL AccuTOF™ time-of-flight mass spectrometer. The orifice operated at ground potential. Nitrogen gas was introduced into the first chamber C1 inlet G1 and allowed to flow out the outlet in electrode E2. A needle electrode N was set to a value sufficient to initiate a gas discharge (typically 900 V to 1,500 V) and electrodes E0, E1, and E2 were set to ground potential. The spectrum of FIG. 9 illustrates background ions in the carrier gas. The ions are primarily formed from impurities in the discharge region chamber C1. Their elemental composition may be assigned from nominal mass measurements as shown in Table 1.

TABLE 1

| Nominal Mass | Composition |
|---|---|
| 26 | $CN^-$ |
| 35 | $^{35}Cl^-$ |
| 37 | $^{37}Cl^-$ |
| 42 | $CNO^-$ |
| 45 | $HCO_2^-$ |
| 46 | $NO_2^-$ |
| 59 | $C_2H_3O_2^-$ |
| 60 | $CO_3^-$ |
| 61 | $HCO_3^-$ |
| 62 | $NO_3^-$ |

Figure 10:
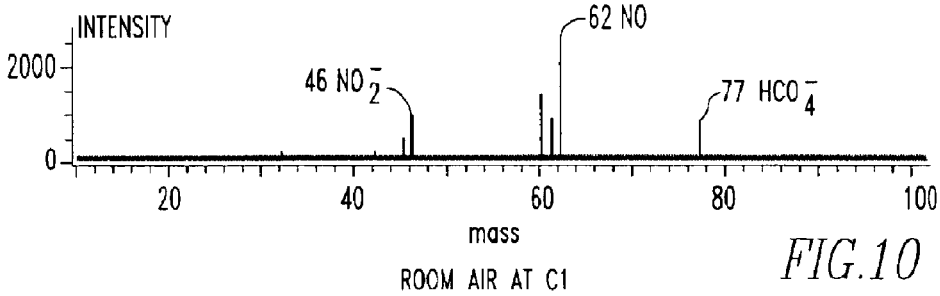
FIG. 10 is a mass spectrum wherein room air is introduced into the nitrogen carrier gas stream in chamber C1 of FIG. 2.
Figure 11:
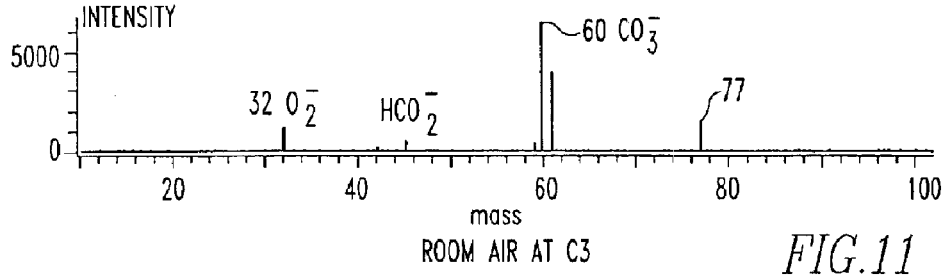
FIG. 11 is a mass spectrum wherein room air is introduced into chamber C3 of FIG. 2.

A benefit of the present invention is shown in FIGS. 10 and 11. FIG. 10 shows the result of injecting 3 cc of room air into the nitrogen stream flowing through inlet G1. Note the high abundance of $NO_2^-$ and $NO_3^-$. In contrast, if 3 cc of room air is injected into chamber C3 through G3, then the primary species formed are $O_2^-$, $HCO_3^-$, $CO_3^-$, $HO_3^-$, and $HCO_4^-$ as shown in FIG. 11. No significant $NO_2^-$ or $NO_3^-$ or related cluster ions are formed in this case.

Figure 12:
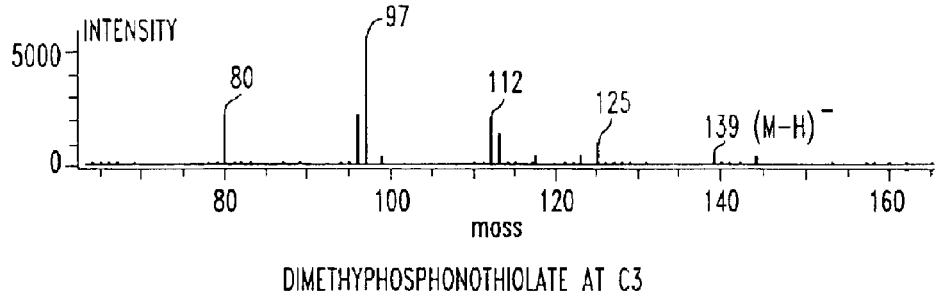
FIG. 12 is a mass spectrum of diethylmethylphosphonothiolate introduced into chamber C3.

If an electrophilic analyte is introduced into inlet G3, characteristic ions can be observed. These ions can result from direct ionization and fragmentation of the analyte, as shown in FIG. 12 for dieylmethylphosphonothioate $[M—C_2H_5]^+$, or they can result from reactions of the analyte ions with other species in chamber C3, as shown for hexafluorobenzene in FIG. 13. This figure shows adduct ions, such as $[M+N]^-$, $[M+O_2]^-$ and $[M+NO_2]^-$ By controlling the neutral environment in chamber C3 (using doping or selective analyte carrier gases or solvents), one can direct the ion formation process.

Figure 13:
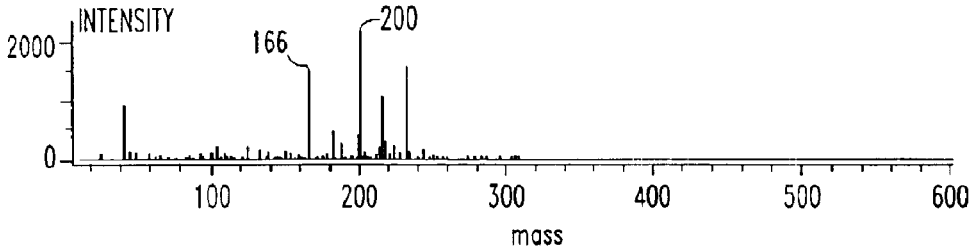
FIG. 13 is a mass spectrum of hexafluorobenzene introduced into chamber C3.
Figure 14:
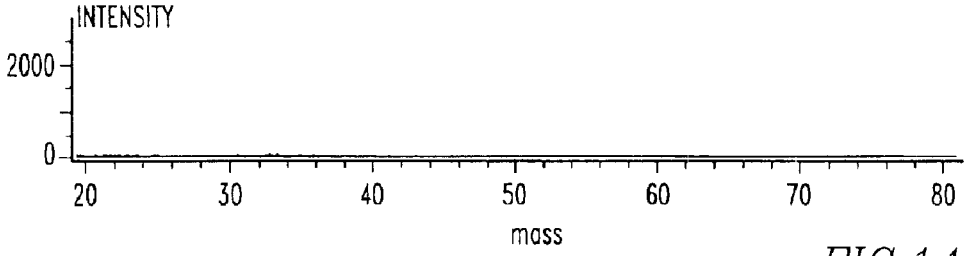
FIG. 14 is a mass spectrum similar to that of FIG. 9 wherein background ions have been eliminated.

In the negative-ion mode, the background ions shown in FIG. 13 can be eliminated from the mass spectrum if either electrodes E1 or E2 is raised to a more positive potential (see FIG. 14 illustrating the spectrum of air with the negative ions trapped). However, an injection of analyte into inlet G3 still produces a large analyte signal because metastable atoms are still present in chamber C3.

As shown in Equation 1, the metastable atoms produce electrons by Penning ionization and the resulting electrons are rapidly cooled to thermal energies by collisions with gas molecules at atmospheric pressure within a few nanoseconds. These electrons can undergo capture by electrophilic analytes to produce analyte ions. The analyte ions can undergo further reactions with species in chamber C3 to produce the resulting mass spectrum. The analytes do not need to be introduced into chamber C3 via port G3. The analytes can be remotely sampled just by aiming the gas stream at the analyte on the surface of a dollar bill, an agricultural leaf, a human fingertip, concrete, asphalt, or an airline ticket, for example.

If the ion source is biased to a more negative potential than the orifice of the mass spectrometer interface, negative ions will be attracted to the orifice and the signal intensity is more than 10 times higher.

Figure 15:
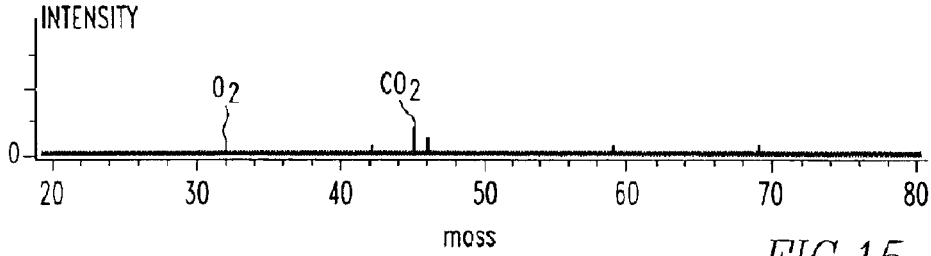
FIG. 15 is a mass spectrum wherein air is introduced into chamber C3.
Figure 16:
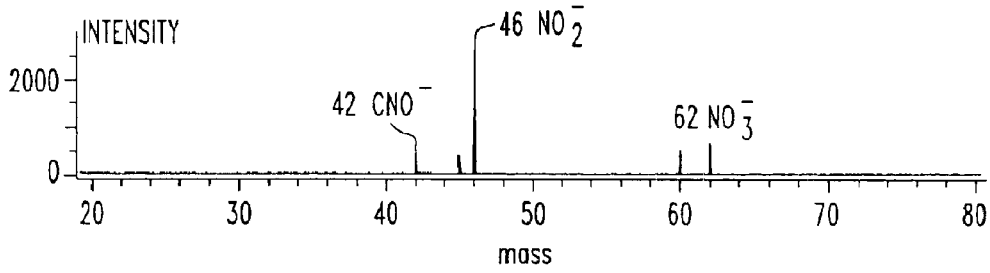
FIG. 16 is a mass spectrum wherein nitrobenzene is introduced into chamber C3.

The excellent selectivity of the present invention is illustrated for the detection of nitromethane. If one injects air into the corona discharge region of a prior art source, large amounts of $NO_2^-$, $NO_3^-$ and related cluster ions are formed. This is shown in FIG. 10 and this result is undesirable if one wishes to detect $NO_2^-$ and $NO_3^-$ produced from a nitro compound, such as nitromethane or nitro explosives. However, if one injects air into chamber C3 in the present invention, no significant $NO_2^-$ and $NO_3^-$ are observed (FIG. 15), but $NO_2^-$ and $NO_3^-$ are the dominant species produced when nitrobenzene is injected through inlet G3 (FIG. 16).

Positive ions can be observed by switching the mass spectrometer polarity.

Figure 17:
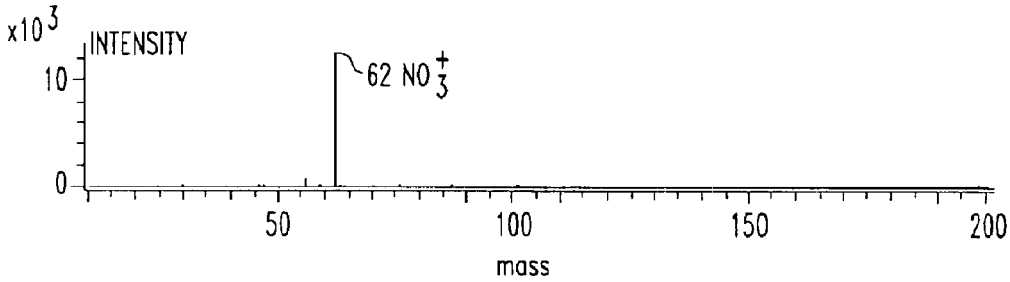
FIGS. 17 and 18 are positive ion mass spectra for nitromethane and nitrobenzene, respectively.
Figure 18:
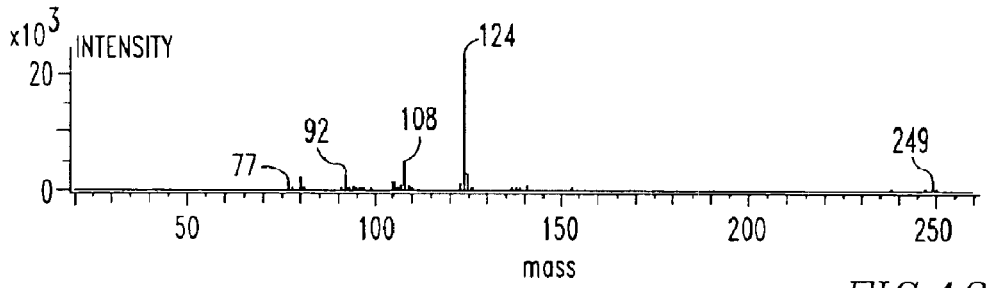

Positive-ion mass spectra for nitromethane (FIG. 17) and nitrobenzene (FIG. 18) show characteristic ions including the most diagnostically useful $[M+H]^+$ion. There is no need to change the potential of the needle electrode N and counter-electrode E0 because metastable atoms are formed with needle electrode N at negative potential as well as at positive potential. Thus, the ion source can be rapidly switched between the positive-ion mode and the negative-ion mode without high-voltage switching, which would require time for reinitiating the gas discharge following a quench. In the positive-ion mode, it is desirable to bias electrodes E1 and E2 such that the potential of electrode E2 is more positive than the potential of the orifice, thus increasing the ion current at the orifice.

Other modes of operation are possible. The electrons produced by the discharge in chamber C1 can be introduced onto chamber C2 and cooled to thermal energies for electron capture by analyte molecules in chamber C3. A related experiment was reported by Leymarie and coworkers (N. Leymarie, J.-C. Tabet, and M. Bertrand, presented at the Annual Meeting of the American Society of Mass Spectrometry, 2000) for a metastable atom ion source operated at subambient pressures and connected to a conventional high-vacuum mass spectrometer ion source. However, this report required a reduced-pressure source and did not describe the use of the ion source at atmospheric pressure for combination with an API mass spectrometer or an ion mobility mass spectrometer. The present invention makes use of the superior electron cooling efficiency of an atmospheric pressure cooling chamber C2. In one implementation, a gas, for example, $CO_2$, that can be ionized by the metastable atoms is introduced into chamber C2 where the emitted electrons are further cooled.

Figure 3:
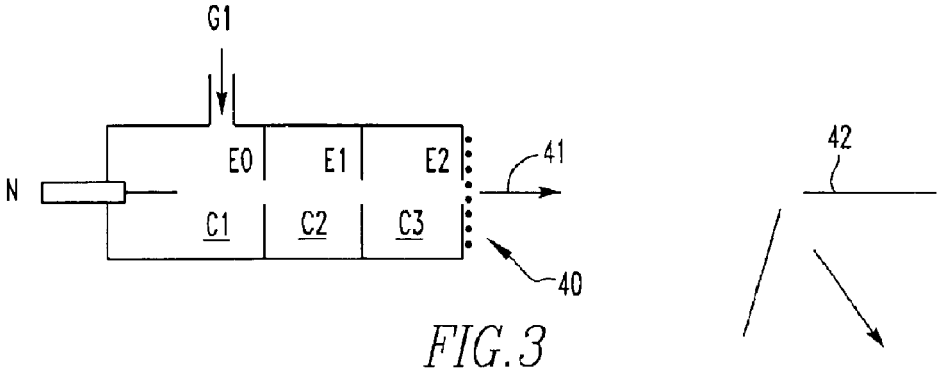
FIG. 3 is a schematic diagram of an atmospheric pressure source or device comprising three chambers followed by a grid for converting metastable species to electrons.
Figure 4:
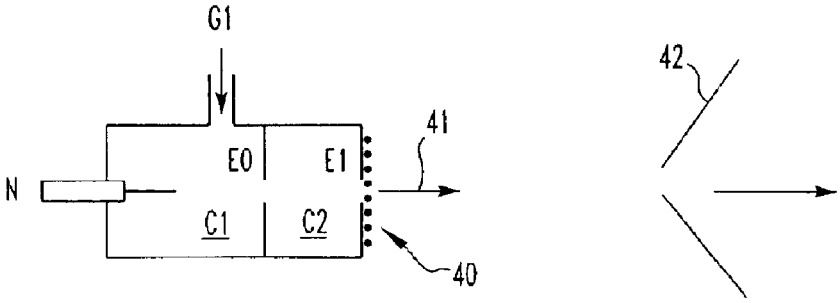
FIG. 4 is a schematic diagram of a simplified atmospheric pressure device having only two chambers.

FIGS. 3 and 4 schematically show atmospheric pressure interfaces wherein a copper mesh plate 40 is used to produce electrons from metastable species 41. It is known that metastable atoms and Rydberg atoms release electrons from a conductive mesh. The mesh can be maintained at a potential, which is negative with respect to the orifice to the mass spectrometer interface 42. The negative potential repels electrons away from the grid or mesh so the electrons ionize the analyte. In this case the analyte is not introduced into chamber C3 but is analyzed in a "sniffer" mode by ionization in the open space between the interface and the mass spectrometer. The space is near ground potential or at least not in an intense electric field. This setup is especially useful for negative ion mass spectrometry, but is also useful for positive ion mass spectrometry. The mesh can also be biased positive with respect to E2 to focus positively charged species such as a positron or proton, for example.

Figure 19:
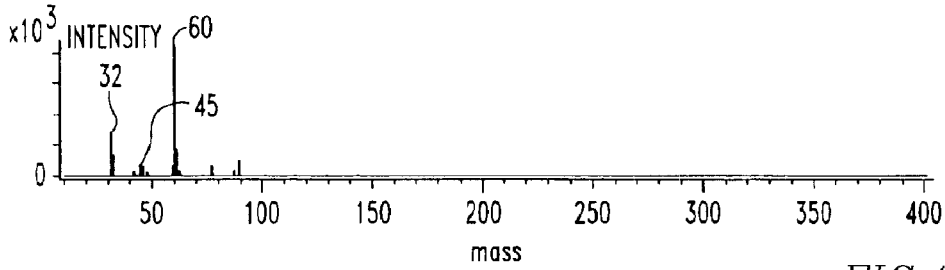
FIG. 19 is a mass spectrum of air using the interface shown schematically in FIG. 3.
Figure 20:
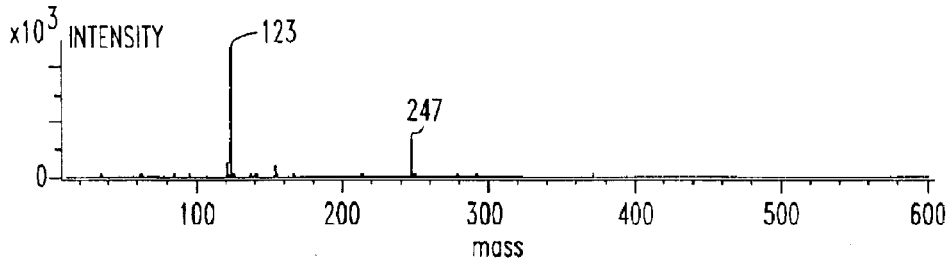
FIG. 20 is a mass spectrum of ethymethyphosphonate using the interface shown schematically in FIG. 3.
Figure 21:
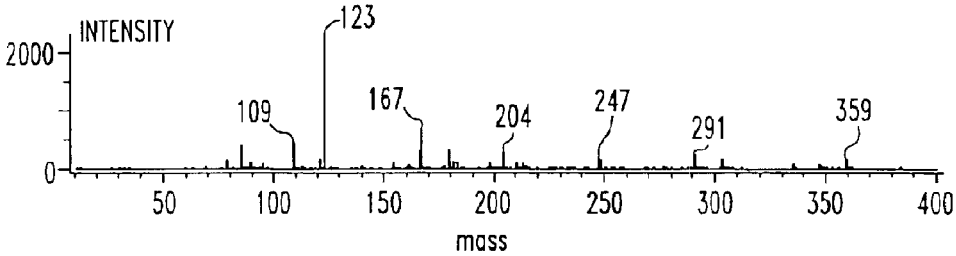
FIG. 21 is a mass spectrum of diethylmethylphosphonate (DEMP) using the interface shown schematically in FIG. 3.
Figure 22:
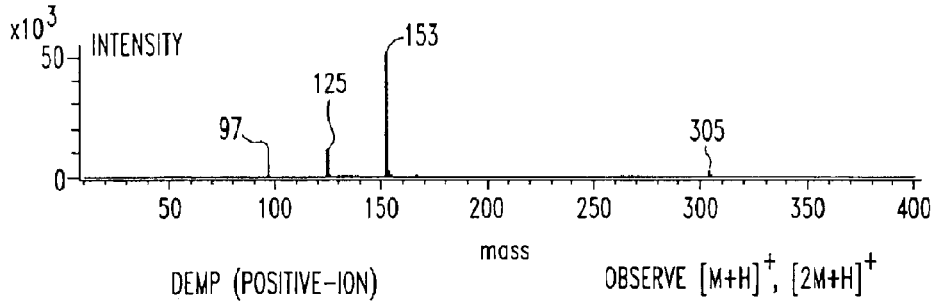
FIG. 22 is a mass spectrum of DEMP (positive ion) using the interface shown schematically in FIG. 3.

In the "sniffer" mode, air is always present. The spectra shown in FIG. 19 displays the background spectra of air in the negative ion mode. The spectra for ethylmethylphosphonate and diethylmethylphosphonate (shown in FIGS. 20 and 21) were generated by placing an open vial of the analyte in the space near the outlet from the atmospheric pressure interface and the inlet to the mass spectrometer. The positive ion mode spectra for diethylmethylphosphonate (shown in FIG. 22) was obtained in the same way.

Figure 23:
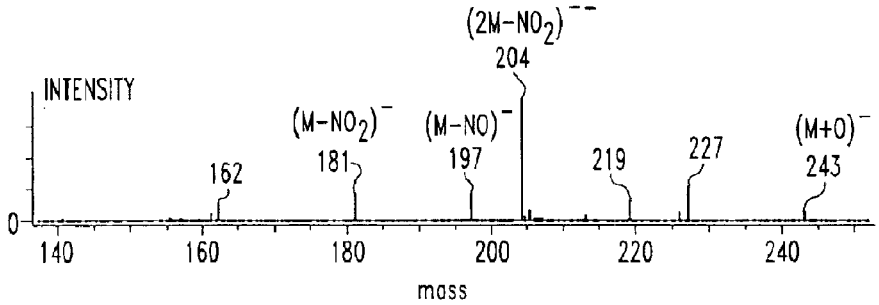
FIG. 23 is a mass spectrum of TNT (negative ion) using the interface shown schematically in FIG. 3.
Figure 24A:
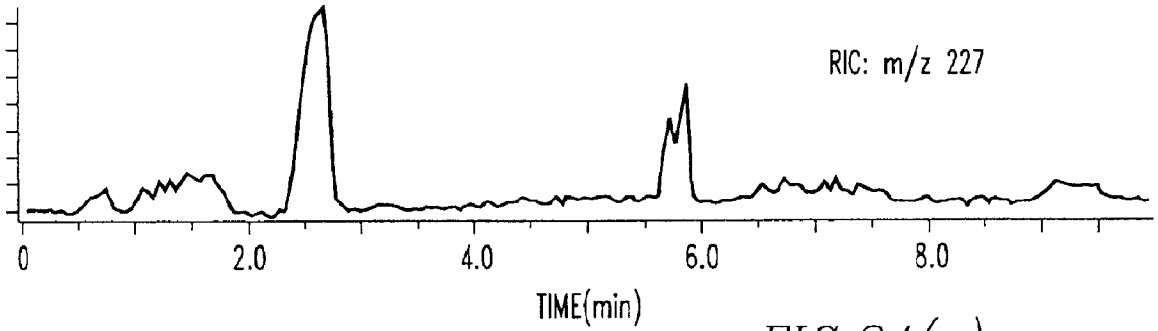
FIG. 24(a) is a mass spectrum of TNT deposited on an airline-boarding pass and FIG. 24(b) is the mass spectrum from the same boarding pass. Positive variations away from the baseline occur when a boarding pass is brought into the vicinity of the source.
Figure 24B:
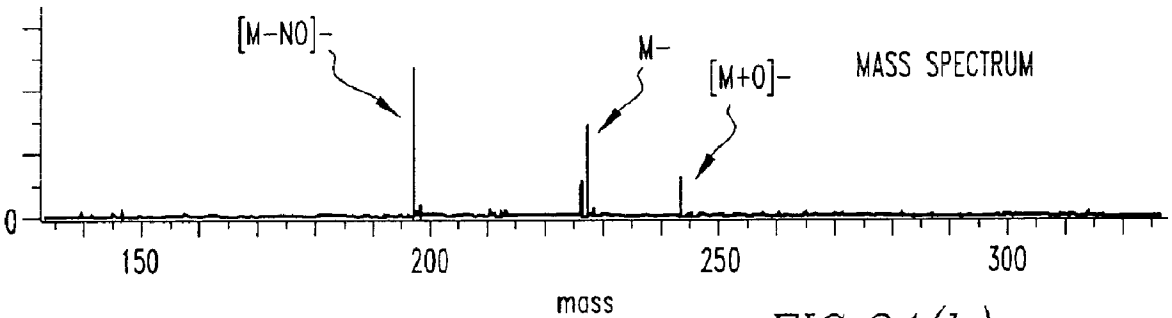

The negative ion spectra for TNT is shown in FIG. 23. In a further study, 700 nanograms of TNT were dissolved and placed on an airline boarding pass and dried for a week. The pass was placed in front of an atmospheric pressure interface in the "sniffer" mode with a negative potential grid. The mass spectrum (FIG. 24(b) and the IMS spectrum (FIG. 24(a)) were observed.

Figure 5:
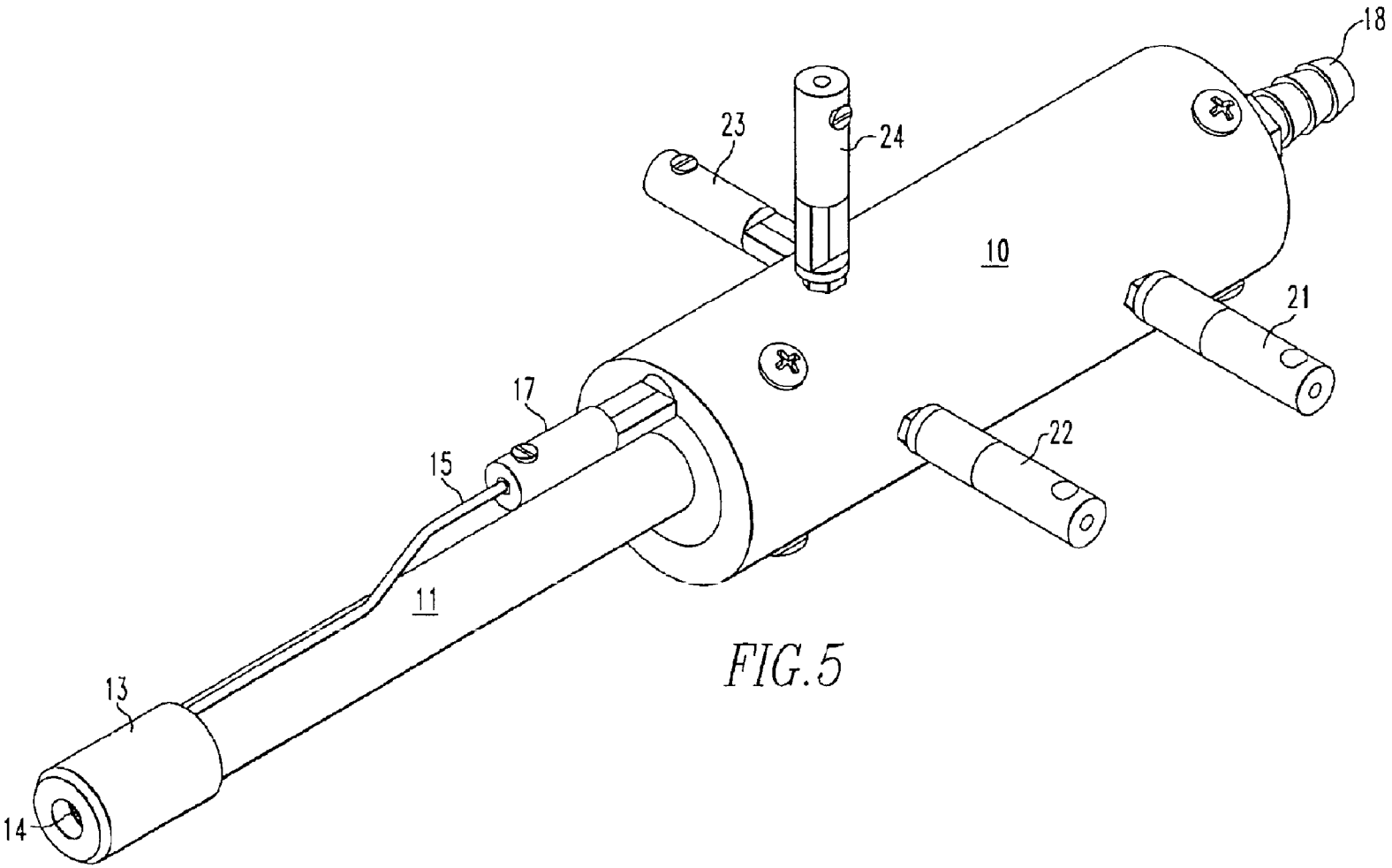
FIG. 5 is a perspective view of an atmospheric pressure interface or device according to the present invention at scale 2:1.

Referring now to FIG. 5, a physical implementation of an atmospheric pressure ion device according to the present invention (as schematically shown in FIG. 3) may comprise a tubular non-conductive casing 10 which may be fabricated from a Teflon®-type plastic (good temperature resistance), a ceramic material, or other non-conductive material. Extending from one end of the casing is a disposable glass tube insert 11 with a non-conductive end piece 13 that serves to hold a mesh electrode or grid 14 in place. The mesh electrode 14 is connected by an insulated wire 15 to a micro-jack 17 on the casing. At the opposite end of the casing 10 is a carrier gas inlet comprising a connector 18 with a corrugated surface for holding a flexible tube slide thereon. Micro-jacks 21, 22, 23, and 24 are threaded in the casing for connecting leads from a power supply to the various electrodes within the casing 10.

Referring now to FIG. 6, the interior of the casing is divided into first and second chambers. At each axial end, a hollow plug is fixed to the casing. At the inlet end, a plug 26 has threads for receiving the inlet connector 18. At the outlet end, a plug 27 is provided with interior annular grooves for receiving Viton O-rings 38 that seal against the exterior surface of the glass tube insert 11. Non-conductive spacer 30 holds the needle electrode 31 which is connected to micro-jack 21 and defines a first chamber in which a corona or glow electrical discharge is created. A conductive spacer and electrode baffle 32 are positioned within the casing and adjacent to the non-conductive spacer supporting the needle. The conductive spacer 32 is connected to micro-jack 23. A non-conductive spacer 33 is positioned within the casing and is adjacent to the conductive spacer 32 to define a second chamber. Another conductive spacer and electrode baffle 34 are positioned adjacent to the non-conductive spacer 33 to define the axial outlet end of the second chamber. The conductive spacer 34 abuts the glass tube insert 11. This conductive spacer is connected to micro-jack 22. The micro-jack 24 is in communication with an electrical conduit that runs axially to the outlet end of the casing where it connects to a micro-jack 17.

Referring to FIG. 7, the end of the glass tube with the non-conductive end piece 13 is shown in more detail. The nonconductive end piece 13 spaces the grid from direct contact making it difficult to come into contact with the high voltage on the grid. The hole in the end piece allows the escape of the excited-state gas to ionize the analyte. A copper washer 39 (see FIG. 7) abuts the end of the glass tube and is soldered to lead 15. Held against the washer is a grid electrode 14. The hollow glass tube 11 and grid electrode 14 define a third chamber.

Figure 8:
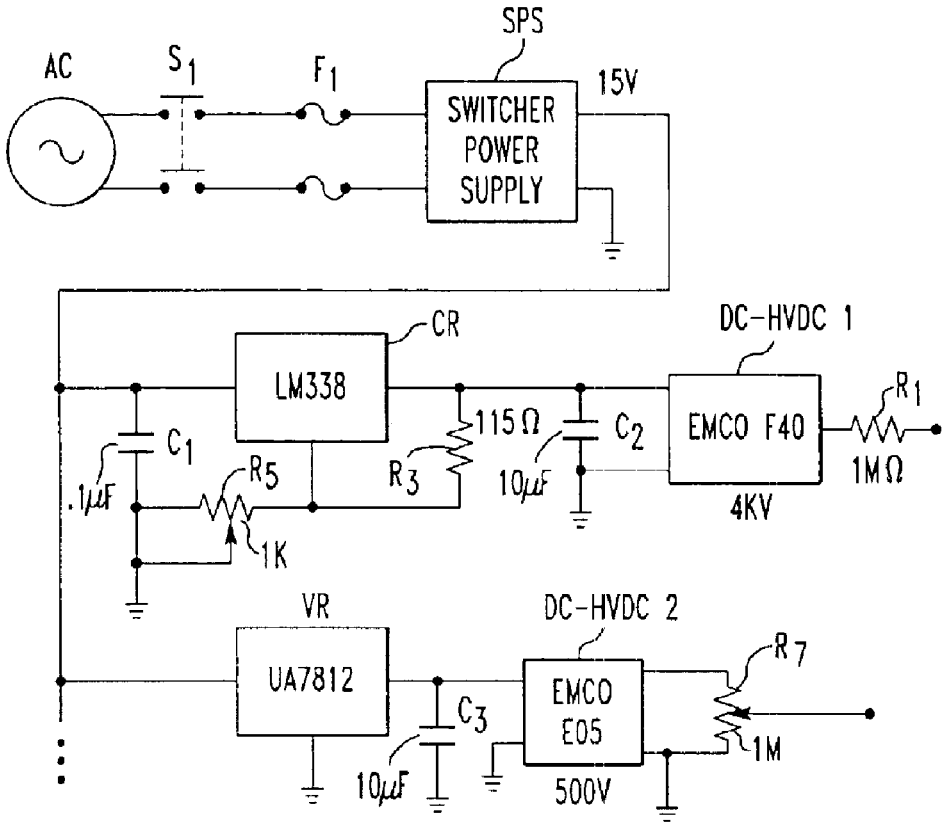
FIG. 8 is a schematic circuit diagram of a power supply for an atmospheric pressure device or source according to the present invention.

Referring to FIG. 8, an example of a power supply for an atmospheric pressure ion source is shown schematically. AC current passes switch $S_1$ and fuse $F_1$ and is applied to switcher power supply SPS. The 15 volt DC output is applied across filter capacitor $C_1$ to current regulator CR. The regulated current is applied across filter capacitor $C_2$ to the high voltage direct current converter DC-HVDC. The high voltage of this device is applied through current limit resistor $R_1$ to the electrode for creating a corona or glow discharge. The 15 volt output is also applied to a plurality of general purpose high current positive voltage regulators VR. The output of the voltage regulators is applied across filter capacitor $C_3$ to pass current to high voltage direct converters DC-HVDC$_2$. The output of the converters is applied to potentiometers $R_7$ enabling adjustment of the potential on the lens electrodes. Those skilled in power supply design will understand how to configure a circuit for negative output potentials.

The atmospheric pressure ion source described herein is useful for the introduction of ions into mass spectrometers and ion mobility spectrometers for the detection and identification of analytes of interest, such as drugs, explosives, chemical weapons, toxic industrial materials, and the like. It is non-radioactive and provides rapid sampling of gas and vapor in headspace sampling. It also permits rapid and direct sampling of chemicals on surfaces. This feature makes the ion source described herein a very useful replacement for a radioactive source on IMS detectors.

It can be useful to simultaneously use more than one ion source or device as described herein. For example, Applicants have conducted experiments wherein two ion sources were simultaneously used to provide ions to a mass spectrometer. In one case, acetone was analyzed in the positive ion mode with two ion sources. The ion current using both sources was approximately the total of the ion currents using either source individually. In another experiment, oxygen ions were detected in the negative ion mode. Again, the ion current using both sources was approximately the total of the ion currents using either source individually.

As used herein, an "atmospheric ionization source" is one that does not require a vacuum pump. Of course, the analyzer (mass spectrometer) may require vacuum pumps, but the ions are formed at pressures somewhat above and below atmospheric pressure.

Having thus described our invention in the detail and particularity required by the Patent Laws, what is desired protected by Letters Patent is set forth in the following claims.

What is claimed is:

[1. A non-radioactive atmospheric pressure device for ionization of analytes comprising:

a first atmospheric pressure chamber having an inlet for carrier gas, a first electrode at one end, and a counter-electrode at the other end for creating an electrical discharge in the carrier gas creating metastable neutral excited-state species;

a second atmospheric pressure chamber adjacent the first chamber and having a port into the first chamber at one end and having an electrode at the other end and an outlet port for the carrier gas, the ports being sized to restrict flow, said first electrode and ports being substantially aligned; and means for contacting gas containing excited-state species flowing out of the outlet port with an analyte at atmospheric pressure near ground potential.]

[2. A non-radioactive atmospheric pressure device for ionization of analytes comprising:

a first atmospheric pressure chamber having an inlet for carrier gas, a first electrode therein, and a counter-electrode for creating an electrical discharge in the carrier gas creating metastable neutral excited-state species;

a second atmospheric pressure chamber adjacent the first chamber and having a port into the first chamber at one end and an electrode at the other end;

a third atmospheric pressure chamber adjacent the second chamber and having a port into the second chamber and an outlet port for the carrier gas, said first electrode, and ports being more or less aligned; and means for contacting gas containing excited-state species flowing out of the outlet port with an analyte at atmospheric pressure near ground potential.]

[3. A non-radioactive atmospheric pressure device for ionization of analytes comprising:

a first atmospheric pressure chamber having an inlet for carrier gas, a first electrode at one end, and a counter-electrode at the other end for creating an electrical discharge in the carrier gas creating metastable neutral excited-state species;

a second atmospheric pressure chamber adjacent the first chamber and having a port into the first chamber at one end and having an electrode at the other end, and an outlet port for the carrier gas, the ports being sized to restrict flow; and a grounded or charged grid electrode at the output port for emission of charged particles upon contact with an excited-state species, said first electrode and ports being substantially aligned.]

[4. A non-radioactive atmospheric pressure device for ionization of analytes comprising:

a first atmospheric pressure chamber having an inlet for carrier gas, a first electrode at one end, and a counter-electrode at the other end for creating an electrical discharge in the carrier gas creating metastable neutral excited-state species;

a second atmospheric pressure chamber adjacent the first chamber and having a port into the first chamber at one end and having an electrode at the other end, and an outlet port for the carrier gas, the ports being sized to restrict flow; and a grounded or negatively charged grid electrode at the output port for emission of electrons upon contact with excited-state species, said first electrode and ports being substantially aligned.]

[5. A non-radioactive atmospheric pressure device for ionization of analytes comprising:

a first atmospheric pressure chamber having an inlet for carrier gas, a first electrode therein, and a counter-electrode for creating an electrical discharge in the carrier gas creating metastable neutral excited-state species;

a second atmospheric pressure chamber adjacent the first chamber and having a port into the first chamber at one end and an electrode at the other end;

a third atmospheric pressure chamber adjacent the second chamber and having a port into the second chamber and an outlet port for the carrier gas; and a grounded or negatively charged grid electrode at the output port for emission of electrons upon contact with excited-state species, said first electrode and ports being more or less aligned.]

[6. A non-radioactive atmospheric pressure device for ionization of analytes comprising:

a first atmospheric pressure chamber having an inlet and exhaust for carrier gas, a first electrode therein, and a counter-electrode for creating an electrical discharge in the carrier gas creating metastable neutral excited-state species;

a second atmospheric pressure chamber adjacent the first chamber and having a flow restricting port into the first chamber at one end and an electrode at the other end, and having an inlet and outlet for optional cooling of reactant gases;

a third atmospheric pressure chamber adjacent the second chamber and having a flow restricting port into the second chamber and having an inlet and outlet for analyte gas or vapor; and an outlet port for ionized products of the interaction of the carrier gas and the analyte gas or vapor, said first electrode and ports being more or less aligned.]

[7. A non-radioactive atmospheric pressure device for ionization of analytes comprising:

a first atmospheric pressure chamber having an inlet for carrier gas, a first electrode therein, and a counter-electrode for creating an electrical discharge in the carrier gas creating metastable neutral excited-state species;

at least one intermediate atmospheric pressure chamber adjacent the first chamber and one of said intermediate chambers having a flow restricting port into the first chamber and having an inlet for optional cooling of reactant gases;

a final atmospheric pressure chamber adjacent one of said intermediate chambers and having a port into an intermediate chamber, and having an inlet for analyte gas or vapor; and an outlet port for ionized products of the interaction of the carrier gas and the analyte gas or vapor, said first electrode and ports being substantially aligned.]

[8. The device according to any one of claims 1 to 5, further comprising means for introducing a gas into the second chamber which is capable of being ionized by the excited-state species created in the first chamber to produce positive ions and electrons such that the electrons are thermalized by further collisions.]

[9. The device according to any one of claim 1, 2, 6, or 7, further comprising a grid arranged for contact with excited-state species.]

[10. The device according to any one of claims 1 to 7, further comprising means for adjusting the potentials on said electrodes to control the speed of ionizing electron energy.]

[11. The device according to any one of claims 1 to 7, comprising means for adjusting the carrier gas pressure to control the speed of ionizing electron energy since electrons embedded in the gas stream will be carried along and accelerated by changing gas pressures.]

[12. The device according to any one of claims 1 to 6, wherein the electrode in the second chamber is a lens electrode.]

[13. The device according to any one of claims 1 to 7, wherein the electrode potentials are adjusted to promote production of positive analyte, fragment, or adduct ions.]

[14. The device according to any one of claims 1 to 6, wherein the electrode potentials are adjusted to promote production of negative analyte, fragment, or adduct ions.]

[15. The device according to any one of claims 1 to 6, wherein the electrode in the second chamber is biased at a negative potential to trap positive ions and to repel free electrons whereby to place the ion source in the negative ion mode.]

[16. The device according to any one of claims 1 to 6, wherein the electrode in the second chamber is biased at a positive potential to trap negative ions and electrons and repel positive ion species and allow excited-state species to pass whereby to place the ion source in the positive ion mode.]

[17. A method of producing analyte, analyte fragment, and/or analyte adduct ions for spectrographic analysis comprising the steps of:

introducing a carrier gas into a first atmospheric pressure chamber having a first electrode at one end and a counter-electrode at the other end and applying a potential to the first electrode and counter-electrodes to cause an electrical discharge in the carrier gas creating metastable neutral excited-state species;

introducing the carrier gas and metastable species into a second atmospheric pressure chamber wherein the metastable species interacts with the carrier gas to produce positive ions and thermalized electrons; and directing the carrier gas from the second chamber into contact with the analyte maintained at atmospheric pressure and near ground potential to form analyte ions, analyte fragment ions, and/or analyte adduct ions.]

[18. The method according to claim 17, wherein the carrier gas is helium and the first electrode is maintained more negative than about minus 400 volts and the counter-electrode is maintained near ground potential.]

[19. The method according to claim 17, wherein the carrier gas is helium and the first electrode is maintained more positive than about positive 400 volts and the counter-electrode is maintained near ground potential.]

[20. The method according to claim 17, wherein the carrier gas is nitrogen and the first electrode is more negative than about minus 1,200 volts and the counter-electrode is maintained near ground potential.]

[21. The method according to claim 17, wherein the carrier gas is nitrogen and the first electrode is made more positive than about 1,200 volts and the counter-electrode is maintained near ground potential.]

[22. A method of producing analyte, analyte fragment, and/or analyte adduct ions for spectrographic analysis comprising the steps of:

introducing a carrier gas into a first atmospheric pressure chamber having a first electrode at one end and a counter-electrode at the other end and applying a potential to the first electrode and counter-electrodes to cause an electrical discharge in the carrier gas creating metastable neutral excited-state species;

introducing the carrier gas and metastable species into a second atmospheric pressure chamber wherein the metastable species interacts with the carrier gas to produce positive ions and thermalized electrons;

introducing the carrier gas, positive ions, and/or thermalized electrons into a third atmospheric pressure chamber; and introducing a gaseous or vaporized analyte into the third chamber to form analyte ions, analyte fragment ions, and/or analyte adduct ions.]

[23. The method according to claim 22, wherein the carrier gas is helium, the first electrode is maintained more negative than about minus 400 volts, and the counter-electrode is maintained near ground potential.]

[24. The method according to claim 22, wherein the carrier gas is helium, the first electrode is maintained more positive than positive 400 volts, and the counter-electrode is maintained near ground potential.]

[25. The method according to claim 22, wherein the carrier gas is nitrogen, the first electrode is made more negative than about minus 1,200 volts, and the counter-electrode is maintained near ground potential.]

[26. The method according to claim 22, wherein the carrier gas is nitrogen, the first electrode is made more positive than about positive 1,200 volts, and the counter-electrode is maintained near ground potential.]

[27. A method of producing analyte, analyte fragment, and/or analyte adduct ions for spectrographic analysis comprising the steps of:

introducing a carrier gas into a first atmospheric pressure chamber having a first electrode at one end and a counter-electrode at the other end and applying a potential to the first electrode, and counter-electrodes to cause an electrical discharge in the carrier gas creating metastable neutral excited-state species;

directing the carrier gas and metastable species at a grid electrode biased to generate electrons or ions; and then directing the carrier gas into contact with the analyte at atmospheric pressure to form analyte ions, analyte fragment ions, and/or analyte adduct ions.]

[28. A method of producing analyte, analyte fragment, and/or analyte adduct ions for spectrographic analysis of analytes on a surface at near atmospheric temperature and ground potential comprising the steps of:

introducing a carrier gas into a first atmospheric pressure chamber having a first electrode at one end and a counter-electrode at the other end and applying a potential to the first electrode and counter-electrodes to cause an electrical discharge in the carrier gas creating metastable neutral excited-state species;

directing the carrier gas and metastable species at a grid electrode biased at a negative potential to cause emission of electrons when struck by a metastable species; and then directing the carrier gas and emitted electrons against a surface at atmospheric pressure and near ground potential to form analyte ions, analyte fragment ions, and/or analyte adduct ions.]

[29. A method of replacing a radioactive source in a charged particle detector comprising:

removing the radioactive source and replacing it with a non-radioactive atmospheric pressure device for ionization of analytes comprising:

a first atmospheric pressure chamber having an inlet for carrier gas, a first electrode therein, and a counter-electrode for creating an electrical discharge in the carrier gas creating metastable neutral excited-state species; and at least one intermediate atmospheric pressure chamber in communication with the first chamber and having a flow restricting port into the first chamber and having an inlet for analyte gas or vapor, and an outlet port in communication with the charged particle detector.]

[30. A device according to claims 1 to 7, wherein the electrode at the other end of the second chamber is connected to a power supply that can switch polarity of the electrode without changing the polarity of the first and counter-electrode, whereby the device can be rapidly changed from a positive ion to a negative ion mode and vice versa.]

[31. A method of producing analyte, analyte fragment, and/or analyte adduct ions for spectrographic analysis of analytes on a surface at near atmospheric temperature and ground potential comprising the steps of simultaneously using more than one non-radioactive atmospheric pressure ionization device as described in claim 1.]

[32. A non-radioactive atmospheric pressure device for ionization of analytes comprising:

an atmospheric pressure chamber having an inlet for carrier gas and means for creating metastable neutral excited-state species in the carrier gas; and means for contacting gas containing excited-state species with an analyte at atmospheric pressure near ground potential.]

[33. A non-radioactive atmospheric pressure device for ionization of analytes comprising:

an atmospheric pressure chamber having an inlet for carrier gas and means for creating metastable neutral excited-state species in the carrier gas;

a grounded or charged grid electrode for emission of charged particles upon contact with an excited-state species; and means for contacting gas containing said charged particles with an analyte at atmospheric pressure near ground potential.]

[34. A method of producing analyte, analyte fragment and/or analyte adduct ions for spectrographic analysis comprising the steps of:

introducing a carrier gas into an atmospheric pressure chamber and creating metastable neutral excited-state species in said carrier gas; and directing the carrier gas from the chamber into contact with the analyte maintained at atmospheric pressure and near ground potential to form analyte ions, analyte fragment ions, and/or analyte adduct ions.]

[35. A method of producing analyte, analyte fragment, and/or analyte adduct ions for spectrographic analysis comprising the steps of:

introducing a carrier gas into an atmospheric pressure chamber for creating metastable neutral excited-state species;

directing the carrier gas and metastable species at a grid electrode biased to generate electrons or ions; and then directing the carrier gas into contact with the analyte at atmospheric pressure to form analyte ions, analyte fragment ions, and/or analyte adduct ions.]

*36. A non-radioactive atmospheric pressure device for desorption and ionization of analytes comprising:*

*a chamber; a first electrode and a second electrode spaced apart from the first electrode, wherein at least a portion of each of the first and second electrodes are positioned in the chamber;*

*at least one power supply configured to energize the first and second electrode to provide current between the first and second electrodes to generate a glow discharge;*

*a resistor configured to limit current supplied to the glow discharge, the resistor having a resistance sufficiently high to avoid arcing between the first and second electrodes; and*

*a gas inlet in the chamber to receive carrier gas from a supply of carrier gas configured to introduce carrier gas to the glow discharge to create effluents of the carrier gas for desorption and ionization of analytes for analysis.*

*37. The device of claim 36, wherein the supply of carrier gas is a supply of helium.*

*38. The device of claim 37, wherein the supply of helium is configured to introduce helium to the glow discharge to create ions, electrons, and excited species of the helium, and wherein, the ions, electrons, and excited species are introduced to analytes to effect desorption and ionization of analytes for analysis.*

*39. The device of claim 36, wherein analytes are selected from the group consisting of a gas, a liquid, and a solid.*

*40. The device of claim 36, wherein the effluents are conducted to the analytes through a second chamber in the shape of a tube.*

*41. The device of claim 36, wherein a large potential is required to initiate the glow discharge but a lower voltage is required to sustain the glow discharge.*

*42. The device of claim 41, wherein the lower voltage is required to sustain the glow discharge following break down.*

* * * * *

UNITED STATES PATENT AND TRADEMARK OFFICE

CERTIFICATE OF CORRECTION

PATENT NO. : RE44,603 E
APPLICATION NO. : 13/278778
DATED : November 19, 2013
INVENTOR(S) : Cody et al.

It is certified that error appears in the above-identified patent and that said Letters Patent is hereby corrected as shown below:

In the Specification

Column 1, line 7, above the heading "CROSS REFERENCE TO RELATED APPLICATION" insert --Notice: More than one reissue application has been filed for the reissue of patent 6,949,741. The reissue applications are 11/858,682, 13/278,778 and 14/040,335.--.

Signed and Sealed this
Twenty-third Day of June, 2015

Michelle K. Lee

Michelle K. Lee
*Director of the United States Patent and Trademark Office*